United States Patent [19]

Inoue et al.

[11] 4,399,017
[45] Aug. 16, 1983

[54] GAS SENSOR HAVING LEAD WIRES EXTENDING IN INSULATING AND HERMETICALLY SEALED HOLDER

[75] Inventors: Yasuhide Inoue; Kenji Ikezawa; Shinji Kimura, all of Yokosuka, Japan

[73] Assignee: Nissan Motor Company, Limited, Yokohama, Japan

[21] Appl. No.: 338,539

[22] Filed: Jan. 11, 1982

[30] Foreign Application Priority Data

Jan. 19, 1981 [JP] Japan .................................. 56-5115

[51] Int. Cl.³ .............................................. G01N 27/58
[52] U.S. Cl. ........................................ 204/425; 422/94
[58] Field of Search .............. 204/195 S, 1 S; 338/34; 422/94, 95, 96, 97, 98

[56] References Cited

U.S. PATENT DOCUMENTS

| | | | |
|---|---|---|---|
| 4,209,377 | 6/1980 | Shinohara et al. | 204/195 S |
| 4,224,113 | 9/1980 | Kimura et al. | 204/1 T |
| 4,264,425 | 4/1981 | Kimura et al. | 204/195 S |
| 4,327,054 | 4/1982 | Yasuda et al. | 422/95 |

FOREIGN PATENT DOCUMENTS

| | | | |
|---|---|---|---|
| 2449887 | 9/1980 | France | 204/195 S |
| 2457486 | 12/1980 | France | 204/195 S |
| 2457488 | 12/1980 | France | 204/195 S |
| 2050628 | 1/1981 | United Kingdom | 204/195 S |
| 2051379 | 1/1981 | United Kingdom | 204/195 S |

*Primary Examiner*—G. L. Kaplan
*Attorney, Agent, or Firm*—Schwartz, Jeffery, Schwaab, Mack, Blumenthal & Koch

[57] ABSTRACT

A gas sensor having a gas sensing element, e.g. a solid electrolyte oxygen concentration cell, attached to a front end of a rod-shaped ceramic holder which is fitted in a tubular metal casing and a short rod-shaped ceramic plug fitted in a rear end portion of the tubular casing so as to leave a space between the rear end of the holder and the plug. Across the space, a plurality of lead wires attached to the sensing element extend through axial holes bored in both the holder and the plug. The space between the holder and the plug and the holes in the plug are filled with a hermetic sealant, which is preferably a lead glass solidified from molten state within the casing, to positively prevent gases subject to measurement from passing through the holes in the holder.

12 Claims, 6 Drawing Figures

GAS SENSOR HAVING LEAD WIRES EXTENDING IN INSULATING AND HERMETICALLY SEALED HOLDER

BACKGROUND OF THE INVENTION

This invention relates to a gas sensor of the type having an electrochemical gas-sensing element to which a plurality of lead wires are attached and a holder assembly including a rod-shaped holder of a heat-resistant and electrically insulating material formed with a plurality of axial holes through which the lead wires extend.

Currently various kinds of gas sensors are used in many fields concerned with high temperature gases such as combustion gases. For example, in the automobile industry it has been popular to use an oxygen sensor, or a carbon monoxide sensor, in an air-fuel ratio control system as a means for producing a feedback signal which is indicative of the concentration of oxygen, or carbon monoxide, in the exhaust gas and hence indicative of an actual air-fuel ratio of a gas mixture supplied to the engine. Oxygen sensors are also employed for controlling the air-fuel ratio in combustion apparatus other than automotive internal combustion engines and for controlling gas atmospheres in industrial furnaces.

Usually the sensitive part of currently used gas sensors is a gas sensing element that operates on an electrochemical principle. For example, an oxygen concentration cell utilizing an oxygen ion conductive solid electrolyte which serves as an oxygen sensing element, and an oxide semiconductor that undergoes a change in its resistivity with a change in the content of a specific substance in an ambient gas atmosphere is useful for producing an oxygen sensing element or a carbon monoxide sensing element. It is a recent trend to construct gas sensing elements in the form of a laminate of very thin layers on a substrate by using either a thin film technique or a thick film technique to thereby reduce the size of the element and enhance its sensitivity.

A practical gas sensor using a gas sensing element of the above described category is constructed so as to fixedly dispose the gas sensing element in a gas atmosphere subject to measurement, usually a hot gas atmosphere, and to measure the output of the sensing element at a location isolated from that gas atmosphere. Usually the gas sensing element is provided with a plurality of thin lead wires. In a typical sensor construction, the gas sensing element is fixed to one end of a rod-shaped holder which is made of a ceramic material such as alumina or mullite and has a plurality of axial holes. The lead wires are respectively passed through the axial holes in the ceramic holder, and the remaining spaces in the holes are filled with a heat-resistant sealant of which the principal component is usually an alumina powder. The ceramic holder is tightly fitted into a tubular metal casing, and the lead wires protruding from the free end of the ceramic holder are respectively connected to thicker wires which are passed through an elongate and axially bored plug formed of either a synthetic rubber or a synthetic resin. Usually the rubber or resin plug is held in axial alignment with the ceramic holder in the metal casing by tightly inserting this plug and an end portion of the metal casing into a metal sleeve.

In practice, however, it is very difficult to realize a truly hermetic seal in the elongate and cross-sectionally narrow holes in the ceramic holder. Besides, it is inevitable that the rubber or resin plug is slightly spaced from the end face of the ceramic holder. Therefore, during use of the gas sensor a small quantity of the gas subject to measurement such as an engine exhaust gas, passes through microscopic interstices in the ceramic sealant in the holes of the ceramic holder to reach the gap between the holder and the rubber or resin plug. Consequently, there occurs an accumulation of carbonaceous solid matter on the end faces of the holder and the plug, sufficient to cause the electrical insulation between the lead wires to lower. Moreover, the lead wires tend to gradually corrode. These phenomena become serious obstacles to accurate measurement of the output of the gas sensing element and significantly shorten the service life of the gas sensor.

SUMMARY OF THE INVENTION

The present invention is concerned with a gas sensor of the type having an electrochemical gas-sensing element to which a plurality of lead wires are attached and a rod-shaped ceramic holder formed with a plurality of axial holes to pass the lead wires therethrough, and it is a primary object of the invention to positively prevent a gas to which the gas-sensing element is exposed from passing through the holes in the rod-shaped holder and consequentially adversely affecting the accuracy of measurement of the output of the gas-sensing element or service life of the sensor.

A gas sensor according to the invention has a tubular metal casing, a rod-shaped holder of a ceramic material formed with a plurality of axial through-holes and tightly fitted in the tubular casing, a gas sensing element which operates on an electrochemical principle and is fixed to a forward end of the rod-shaped holder, a plurality of lead wires which are attached to the gas sensing element and respectively passed through the through-holes in the rod-shaped holder, and a heat-resistant sealant fitted into the through-holes in the rod-shaped holder. The improvement according to the invention resides in that the gas sensor comprises a rod-shaped plug of a ceramic material which is formed with a plurality of axial through-holes and tightly fitted in an end portion of the tubular casing so as to leave a space between the rear end of the rod-shaped holder and the forward end of the plug, the lead wires being respectively passed through the through-holes in the plug across the aforementioned space, and a hermetic sealant which fills the space between the holder and the plug and the through-holes in the plug.

As the hermetic sealant, it is preferred to use a lead glass which is solidified from molten state within the tubular casing. To facilitate complete filling of the through-holes in the plug with the hermetic sealant, the through-holes in the plug are preferably made larger in cross-sectional area than the through-holes in the rod-shaped holder. Also it is preferred that the hermetic sealant is made to intrude into the through-holes in the holder at least in a rear end portion of the holder.

The combination of the bored plug and the hermetic sealant according to the invention positively prevents gases from passing through the axial holes in the rod-shaped holder primarily because the space between the holder and the plug forms a defectless sealant layer. Therefore, a gas sensor according to the invention seldom suffers from unfavorable effects of being subjected to measurement gases, such as deterioration of the insulation between the lead wires or corrosion of the lead wires. Consequently, a gas sensor according to the invention has a long service life and retains an accurate output.

Additional objects, advantages and novel features of the invention are set forth in the description which follows as will be apparent to one of skill in the art.

DESCRIPTION OF THE PREFERRED EMBODIMENTS

Figure 1:
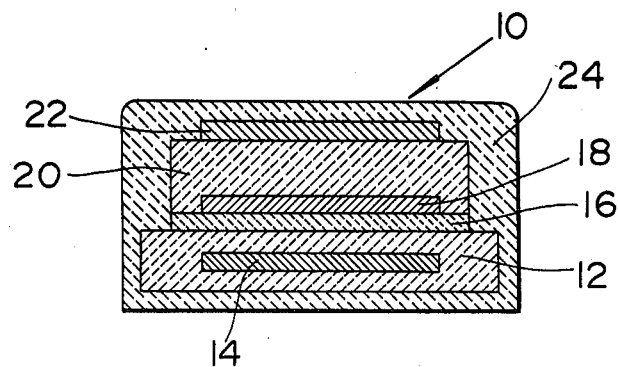
FIG. 1 is a schematic and sectional view of an oxygen sensing element useful in the present invention.

FIG. 1 shows an oxygen sensing element 10 as an example of various kinds of gas sensing elements useful in the present invention. This element 10 is of the oxygen concentration cell type using an oxygen ion conductive solid electrolyte as its principal material.

A structurally basic member of this element 10 is a substrate 12 made of a ceramic material such as alumina. A heater element 14 such as a thin layer of platinum is embedded in the substrate 12 for the purpose of heating the entire sensing element 10 when used in a relatively low temperature gas atmosphere. There is a thin intermediate layer 16 formed of a solid electrolyte on a major surface of the substrate 12, and an inner electrode layer 18 is formed on the outer surface of the intermediate layer 16. This electrode layer 18 is a thin, film-like layer patterned so as not to cover a marginal region of the intermediate layer 16. An oxygen ion conductive solid electrolyte layer 20 is formed so as to cover the electrode layer 18 substantially entirely and, in its marginal region, to make a close contact with the initially uncovered marginal region of the intermediate layer 16. Accordingly the electrode layer 18 is substantially entirely enclosed by the two solid electrolyte layers 16 and 20. The solid electrolyte layer 20 has a microscopically porous structure. The two solid electrolyte layers 16 and 20 may be different in thickness (usually the upper layer 20 is thicker than the intermediate layer 16) but are similar or analogous in material. For example, when the solid electrolyte layer 20 is made of zirconia stabilized with yttria, zirconia is employed as the principal material of the intermediate layer 16 though the auxiliary component of this layer 16 needs not to be yttria and may be calcia for example. An outer electrode layer 22 is formed on the outer surface of the solid electrolyte layer 20. This electrode layer 22, like electrode 18, is a thin, film-like layer and has a microscopically porous structure. Platinum is a typical material for both the inner and outer electrode layers 18 and 22. The outer surfaces of the entire element 10, or the outer surfaces of the laminate (16,18,20,22) formed on the substrate 12, are coated with a protecting layer 24 which is formed of a ceramic material such as spinel and has a porous structure to allow a gas subject to measurement to pass therethrough and arrive at the outer electrode layer 22.

As is known, the oxygen ion conductive solid electrolyte layer 20 and the two electrode layers 18 and 22 constitute an oxygen concentration cell that generates an electromotive force when there is a difference in oxygen partial pressure between the inner electrode side and the outer electrode side of the solid electrolyte layer 20. The intermediate layer 16 is not essential to the concentration cell, but this layer 16 is added with a view to establishing a firm and durable adhesion between the ceramic substrate 12 and the concentration cell part of the element 10. This oxygen sensing element 10 is so designed as to establish a reference oxygen partial pressure at the interface between the inner electrode layer 18 and the solid electrolyte layer 20 by externally supplying a DC current of an adequate intensity to the concentration cell so as to flow through the solid electrolyte layer 20 between the two electrode layers 18 and 22. As disclosed in U.S. Pat. Nos. 4,207,159 and 4,224,113, an oxygen partial pressure of a suitable magnitude can be maintained at the aforementioned interface, while the outer electrode layer 22 is exposed to a gas subject to measurement such as an engine exhaust gas, as a joint effect of migration of oxygen ions through the solid electrolyte layer 20 caused by the flow of the aforementioned current and diffusion of oxygen molecules through the micropores in the solid electrolyte layer 20.

Figure 2:
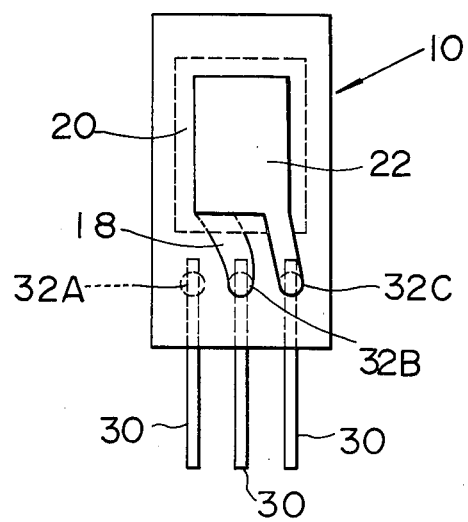
FIG. 2 is a schematic plan view of the same oxygen sensing element.

As shown in FIG. 2, the oxygen sensing element 10 is provided with three lead wires 30, which are usually platinum wires, in order to supply the aforementioned DC current to the concentration cell part and to take out an electromotive force generated by the concentration cell, and also to supply a heating current to the heater 14. At a terminal 32A which is formed by filling up a small hole in the substrate 12 with a conducting material, one of the lead wires 30 is connected with the heater 14. At a similarly formed terminal 32B, another of the lead wires 30 is connected with the inner electrode layer 18. At a third terminal 32C, the third of the lead wires 30 is connected with both the outer electrode layer 22 and the heater 14, so that this lead wire serves as a grounding lead common to the heater 14 and the concentration cell in this element 10. In FIG. 2, the protecting coating layer 24 is omitted from illustration. Actually, this oxygen sensing element 10 can be produced in very small size. For example, the substrate 12 is about 7 mm×10 mm in width and about 1 mm in thickness, and the total thickness of the laminated concentration cell part is smaller than 50 microns. In such a case, the platinum lead wires 30 are about 0.2 mm in diameter.

Figure 3:
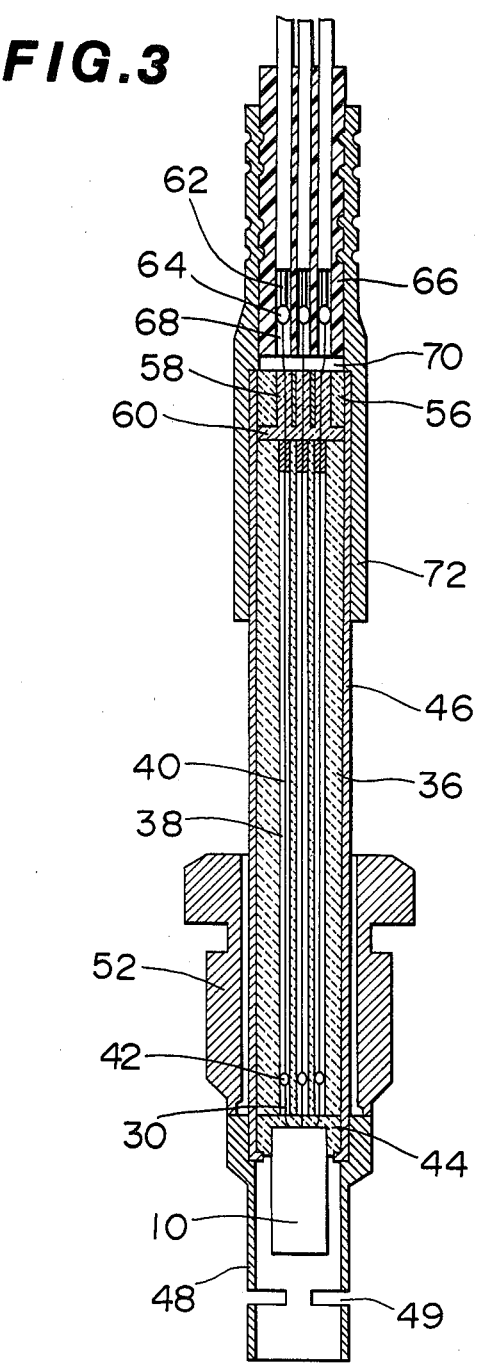
FIG. 3 is a longitudinal sectional view of an embodiment of an oxygen sensor in accordance with the invention.
Figure 4:
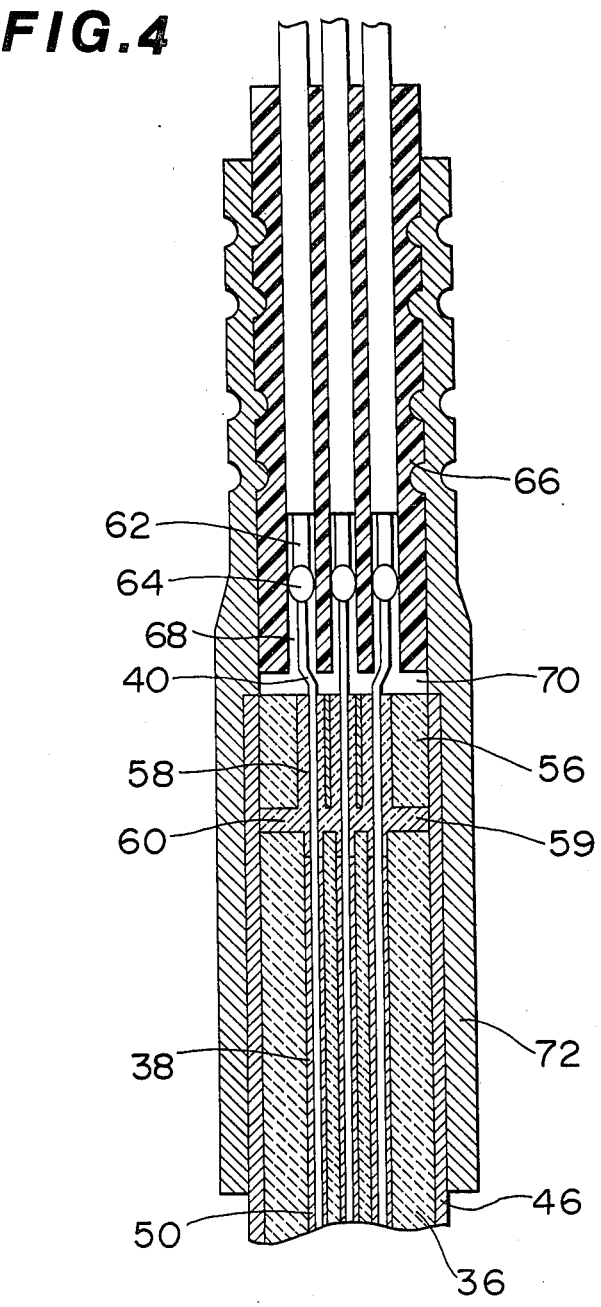
FIG. 4 is a partial enlargement of FIG. 3.

FIGS. 3 and 4 show an oxygen sensor which utilizes the oxygen sensing element 10 of FIGS. 1 and 2 and is designed for use in the exhaust system of an automotive engine to detect the concentration of oxygen in the exhaust gas as an indication of actual air/fuel ratio of a gas mixture supplied to the engine.

The oxygen sensing element 10 is fixedly mounted on an end face of a cylindrical rod 36 of an insulating ceramic material such as mullite by using a ceramic cement 44. The ceramic rod 36 is formed with three axial through-holes 38, and the three platinum lead wires 30 of the oxygen sensing element 10 are respectively welded (indicated at 42) to three nickel wires 40 which extend through the three holes 38 in the rod 36, respectively. The ceramic cement 44 is applied in a quantity more than needed for cementing so as to constitute a seal layer. In this state, the three holes 38 in the ceramic rod 36 are filled with a ceramic sealant 50 of which the principal component is, for instance, an alumina powder. The ceramic rod 36 is tightly inserted into a tubular casing 46 of stainless steel which is longer than the rod 36, and a stainless steel hood 48 formed with apertures 49 is welded to the forward end of the casing 46 so as to enclose the oxygen sensing element 10 therein. A generally tubular metal body 52 having a threaded section and a nut-shaped section is fitted around the casing 46 for attachment of the oxygen sensor to an exhaust manifold or exhaust pipe of an automotive engine.

A cylindrical plug 56 of an insulating ceramic material such as millite, which has the same diameter as the ceramic rod 36 and is formed with three axial throughholes 58 in axial alignment with the holes 38 in the rod 36, is tightly inserted into the tubular casing 46 from its free end so as to leave an adequate gap 59 between the rear end face of the rod 36 and the forward end face of the plug 56. The gap 59 is filled with a hermetic sealant 60, preferably of a lead glass. This sealant 60 intrudes into the three holes 58 in the ceramic plug 56 too.

Indicated at 66 is an outer plug which is formed with three axial holes 68 and is formed of either a synthetic rubber or a synthetic resin such as polytetrafluoroethylene. The nickel lead wires 40 protruding from the rear end of the ceramic plug 56 are respectively soldered (indicated at 64) to three covered copper wires 62, which are inserted into the three holes 68 in the rubber or resin plug 66, respectively. An end portion of the tubular casing 46 containing therein the ceramic rod 36 and the ceramic plug 56 is fitted into one end portion of a metal sleeve 72 and welded thereto. The rubber or resin plug 66 is inserted into the other end portion of the sleeve 72, and the sleeves 72 is circumferentially crimped in this end portion so as to hold the plug 66 with a small gap 70 between the forward end of this plug 66 and the rear end of the ceramic plug 56.

The employment of the ceramic plug 56 and the glass sealant 60 is the essential feature of the present invention. It is preferred that the material of the ceramic plug 56 is the same as or analogous to the material of the ceramic rod 36, and selection of the glass sealant 60 is made such that the glass sealant 60 can well wet both the rod 36 and the plug 56 and strongly adheres to both the rod 36 and the plug 56 when melted in the casing 46 and then allowed to solidify. In the vitrified and solidified state, the glass sealant 60 completely fills up the gap 59 between the ceramic rod 36 and the ceramic plug 56 and provides a hermetic seal. To enhance both the adhesion and sealing, it is desirable that the holes 58 in the plug 56 too are filled with the glass sealant 60. In this regard, it is desirable that these holes 58 are larger in diameter than the holes 38 in the ceramic rod 36.

As the glass sealant 60, it is preferred to use a lead glass, that is, a glass containing PbO as one of principal components thereof. Examples of suitable lead glasses are $PbO-B_2O_3$ base, $PbO-SiO_2$ base, $PbO-ZnO-B_2O_3$ base and $PbO-SiO_2-B_2O_3$ base glasses. These lead glasses are excellent both in chemical stableness and electrical insulation and become very tight when solidified from a molten state. Therefore, these lead glasses are quite suitable as sealant materials in electric or electrochemical devices to be used in corrosive gases such as engine exhaust gases. Furthermore, these lead glasses melt at relatively low temperatures of about 400°–600° C. and accordingly are very convenient for practical use as sealant or adhesive. Because of such low softening temperatures, these lead glasses are rather unsuitable for use as the cement 44 to bond the oxygen sensing element 10 to the ceramic rod 36.

In assembling the oxygen sensor of FIGS. 3 and 4, the ceramic plug 56 and the glass sealant 60 are introduced in the following way. A lead glass as the material of the sealant 60 is prepared in the form of a finely powdered frit, and a slurry is prepared by dispersing the powdered glass frit in a suitable solvent. Before insertion of the ceramic plug 56 into the tubular casing 46, the glass slurry is poured into the space left in the casing 46 above the rear end of the ceramic rod 36, and then the plug 56 is inserted into the casing 46, permitting overflow of the glass slurry through the holes 58 in the plug 56. After drying of the uncompleted sensor to evaporate the liquid component of the slurry poured into the casing 46, the sensor is heated so as to melt the glass frit powder present in the gap 59 between the ceramic rod 36 and the plug 56 and also in the holes 58 of the plug 56. After that the sensor is cooled to allow the molten glass to completely solidify to turn into the glass sealant 60. To ensure complete filling of the gap 59 with the glass sealant 60, care is taken in pouring the glass slurry into the casing 46 such that the volume of the glass produced therefrom will become larger than the volume of the gap 59. By producing the glass sealant 60 in this manner, the glass sealant 60 intrudes into the holes 38 in the ceramic rod 36 too, so that the hermetic sealing in the casing 46 is further ensured. As a result of the hermetic seal by the glass sealant 60, there is no possibility of the exhaust gas intruding into the gap 70 between the casing 46 and the outer plug 66 and unfavorably affecting the lead wires 40 and 62.

The ceramic plug 56 is introduced into the oxygen sensor according to the invention because it is very difficult to directly bond the ceramic rod 36 to the rubber or resin plug 66 by a hermetic sealing layer which strongly adheres to both the ceramic rod 36 and the rubber or resin plug 66.

Figure 5:
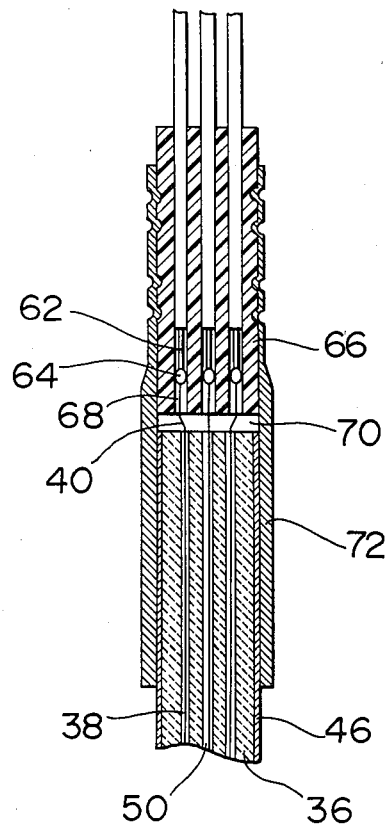
FIG. 5 is a fragmentary and longitudinal sectional view of an oxygen sensor which resembles the sensor of FIG. 3 but is not in accordance with the present invention.

For comparison, FIG. 5 shows a known oxygen sensor which is almost identical with the sensor of FIGS. 3 and 4 except for the absence of the ceramic plug 56 and the glass sealant 60 used in the latter sensor. In the sensor of FIG. 5 the ceramic rod 36 is longer than the counterpart in FIG. 3, so that the rear end of this rod 36 becomes flush with the rear end of the tubular casing 46. There is no sealant between the ceramic rod 36 and the rubber or resin plug 66, and a gap 70 is left between the rear end face of the ceramic rod 36 and the forward end face of the rubber or resin plug 66. The holes 38 in the ceramic rod 36 are filled with the ceramic sealant 50 of which the principal component is usually an alumina powder as mentioned hereinbefore. In practice, however, it is very difficult to establish a truly hermetic seal by using the sealant 50 of such type over the entire length of the holes 38. Therefore, during practical use of this oxygen sensor a certain amount of the exhaust gas passes through the holes 38 in the ceramic rod 36 and intrudes into the aforementioned gap 70, and even into the holes 68 in the outer plug 66. Consequentially there occurs accumulation of carbonaceous solid matter on the rear end face of the ceramic rod 36 and the forward end face of the outer plug 66, which causes the electrical insulation between the three nickel lead wires 40, or between the three copper wires 62, to deteriorate.

Corrosion of these wires 40 and 62 by the influence of the intruded exhaust gas is also probable. For these reasons, it gradually becomes difficult to accurately measure the electromotive force generated at the oxygen element 10.

Figure 6:
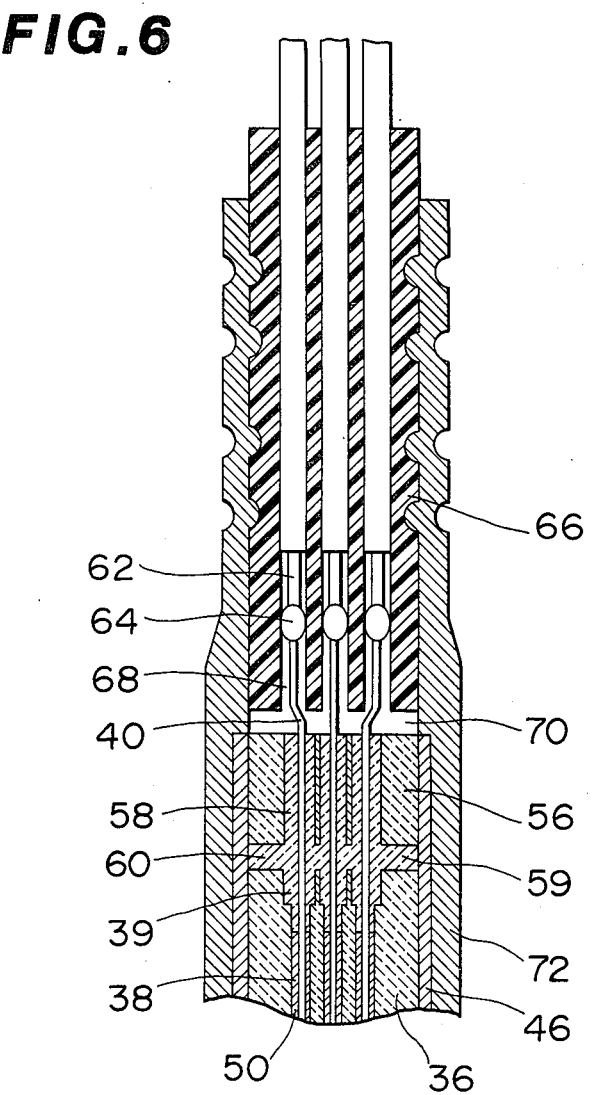
FIG. 6 shows a minor modification of the sensor of FIG. 3 is an enlarged and sectional view similar to FIG. 4.

FIG. 6 shows a preferable modification of the glass sealing part of the oxygen sensor of FIGS. 3 and 4. In this case the holes 58 in the ceramic plug 56 are made larger in diameter than the holes 38 in the ceramic rod 36 as mentioned hereinbefore. Besides, in a rear end portion of the ceramic rod 36, the holes 38 are enlarged in their diameter, as indicated by numeral 39, so as to become comparable to the relatively wide holes 58 in the ceramic plug 56. The enlarged portions 39 of these holes 38 can easily and completely be filled up with the glass sealant 60 by the method described with reference to FIG. 4. The hermetic sealing effect of the glass sealant 60 and adhesion of this sealant to the ceramic rod 36 can further be enhanced by this modification.

It will be understood that the construction of the oxygen sensing element 10 illustrated in FIGS. 1 and 2 is no more than exemplary. There is no particular limitation to the type of the oxygen sensing element for use in an oxygen sensor according to the invention. For example, it is possible to use an oxygen sensing element which resembles the element 10 of FIG. 1 but has a layer of a mixture of metal and its oxide, such as Ni and NiO, adjacent the inner electrode layer as the source of a reference oxygen partial pressure and accordingly does not need the supply of any external current. Also it is possible to use an oxygen sensing element which utilizes an oxide semiconductor such as cobalt oxide or titanium oxide that undergoes a change in its resistance with a change in the oxygen partial pressure in an ambient gas atmosphere. Also it will be understood that the present invention is not limited to oxygen sensors. Various kinds of gas sensors including carbon monoxide sensors and hydrocarbon sensors can be produced by utilizing the present invention.

What is claimed is:

1. In a gas sensor having a tubular metal casing, a rod-shaped holder of a ceramic material formed with a plurality of axial through-holes and tightly fitted in the tubular casing, a gas sensing element which operates on an electrochemical principle and which is fixed to a forward end of the rod-shaped holder, a plurality of lead wires which are attached to the gas sensing element and respectively passed through the through-holes in the rod-shaped holder, and a heat-resistant sealant filled into the through-holes in the holder, the improvement comprising a rod-shaped plug of a ceramic material, said plug being pre-formed with a plurality of axial through-holes and tightly fitted in an end portion of said tubular casing so as to leave a space between the rear end of said holder and the forward end of said plug, said lead wires being respectively passed through said through-holes in said plug across said space, and a hermetic sealant which fills said space between said holder and said plug and said through-holes in said plug, said hermetic sealant comprises a lead glass which is solidified from a molten state within said space and said through-holes in said plug.

2. A gas sensor according to claim 1, wherein said lead glass is selected from the group consisting of PbO-$B_2O_3$ base lead glass, PbO-$SiO_2$ base lead glass, PbO-ZnO-$B_2O_3$ base lead glass and PbO-$SiO_2$-$B_2O_3$ base lead glass.

3. A gas sensor according to claim 1, wherein said through-holes in said plug are larger in cross-sectional area than said through-holes in said holder.

4. A gas sensor according to claim 3, wherein said holder and said plug are made of the same ceramic material.

5. A gas sensor according to claim 1, wherein said hermetic sealant intrudes into a rear end portion of each of said through-holes in said holder.

6. A gas sensor according to claim 1, wherein each of said through-holes in said holder has a cross-sectionally enlarged portion as a rear end portion thereof, said enlarged portion being filled with said hermetic sealant.

7. A gas sensor according to claim 6, wherein said through-holes in said plug are substantially similar in cross-sectional area to the cross-sectionally enlarged portions of said through-holes in said holder.

8. A gas sensor according to claim 1, wherein said heat-resistant sealant comprises a powdered ceramic material as a principal component thereof.

9. A gas sensor according to claim 1, further comprising a sleeve, a portion of which is tightly fitted around a rear end portion of said tubular casing, and a rod-shaped plug of an organic elastic material which is tightly fitted into the remaining portion of said sleeve and formed with a plurality of axial through-holes into which said lead wires extend.

10. A gas sensor according to claim 9, wherein a gap is left between the rear end of said plug of said ceramic material and said plug of said organic material.

11. A gas sensor according to claim 1, wherein said gas sensing element is an oxygen sensing element.

12. A gas sensor according to claim 11, wherein said oxygen sensing element comprises an oxygen ion conductive solid electrolyte and operates on the principle of an oxygen concentration cell.

* * * * *